(12) United States Patent
Burkett et al.

(10) Patent No.: US 10,791,991 B2
(45) Date of Patent: Oct. 6, 2020

(54) INTRAVASCULAR DEVICES, SYSTEMS, AND METHODS

(71) Applicant: Volcano Corporation, San Diego, CA (US)

(72) Inventors: David H. Burkett, Temecula, CA (US); Bret C. Millett, Folsom, CA (US); Paul Douglas Corl, Palo Alto, CA (US)

(73) Assignee: PHILIPS IMAGE GUIDED THERAPY CORPORATION, San Diego, CA (US)

( * ) Notice: Subject to any disclaimer, the term of this patent is extended or adjusted under 35 U.S.C. 154(b) by 531 days.

(21) Appl. No.: 14/143,304

(22) Filed: Dec. 30, 2013

(65) Prior Publication Data

US 2014/0187874 A1 Jul. 3, 2014

Related U.S. Application Data

(60) Provisional application No. 61/777,516, filed on Mar. 12, 2013, provisional application No. 61/747,578, filed on Dec. 31, 2012.

(51) Int. Cl.
*A61B 5/00* (2006.01)
*A61B 5/0215* (2006.01)
(Continued)

(52) U.S. Cl.
CPC .......... *A61B 5/6851* (2013.01); *A61B 5/0215* (2013.01); *A61B 5/026* (2013.01);
(Continued)

(58) Field of Classification Search
CPC ..... A61B 5/021; A61B 5/02141; A61B 5/026; A61B 5/6851; A61B 5/6852; A61N 1/05;
(Continued)

(56) References Cited

U.S. PATENT DOCUMENTS 4,559,951 A * 12/1985 Dahl .................... A61B 5/0422
600/374
5,016,646 A * 5/1991 Gotthardt ............... A61N 1/056
607/122
(Continued)

FOREIGN PATENT DOCUMENTS

EP 0394969 10/1990
JP 7231879 A 9/1995
(Continued)

OTHER PUBLICATIONS

International Search Report and Written Opinion received in corresponding Patent Cooperation Treaty Application No. PCT/US2013/078229 dated Apr. 28, 2014, 12 pages.
(Continued)

*Primary Examiner* — Eugene T Wu

(57) ABSTRACT

Intravascular devices, systems, and methods are disclosed. In some instances, the intravascular device is a guide wire with electrical conductors printed on a solid core wire. In some instances, the electrical conductors are coupled to conductive bands adjacent a proximal portion of the guide wire. Methods of making, manufacturing, and/or assembling such intravascular devices and associated systems are also provided. In certain aspects, guidewires of the invention include a body having an inner core and an outer layer with one or more embedded conductors. The conductors are exposed at one or more locations along the body and a conductive material can be layered over the exposed locations. A sensor can also be coupled to the body via the conductive material at one of the exposed locations.

29 Claims, 10 Drawing Sheets

(51) Int. Cl.
    *A61B 5/026* (2006.01)
    *A61B 8/12* (2006.01)
(52) U.S. Cl.
    CPC ............. *A61B 5/02158* (2013.01); *A61B 8/12* (2013.01); *A61B 2562/12* (2013.01); *A61B 2562/222* (2013.01); *A61B 2562/227* (2013.01); *Y10T 29/49117* (2015.01)
(58) Field of Classification Search
    CPC ....... A61N 1/048; A61M 25/00; A61M 25/01; A61M 25/09; A61M 2025/09133; A61M 2025/09141; A61M 2025/09033; A61M 2025/09175
    See application file for complete search history.

(56) References Cited

U.S. PATENT DOCUMENTS

| | | | |
|---|---|---|---|
| 5,125,137 A | | 6/1992 | Corl et al. |
| 5,873,835 A | | 2/1999 | Hastings et al. |
| 5,882,722 A | | 3/1999 | Kydd |
| 5,991,650 A | * | 11/1999 | Swanson ............... A61B 5/0422 374/E1.005 |
| 6,032,061 A | * | 2/2000 | Koblish ................ A61L 29/085 600/372 |
| 6,036,889 A | | 3/2000 | Kydd |
| 6,106,476 A | * | 8/2000 | Corl ..................... A61B 5/0215 600/486 |
| 6,208,881 B1 | * | 3/2001 | Champeau ........... A61B 5/6852 600/374 |
| 6,329,069 B1 | | 12/2001 | Azizi |
| 6,551,250 B2 | | 4/2003 | Khalll |
| 7,039,470 B1 | * | 5/2006 | Wessman ................. A61N 1/05 607/122 |
| 9,351,687 B2 | | 5/2016 | Burkett |
| 2001/0003790 A1 | | 6/2001 | Ben-Haim et al. |
| 2002/0103445 A1 | | 8/2002 | Rahdert et al. |
| 2004/0039434 A1 | * | 2/2004 | Schrom ................. A61N 1/0551 607/118 |
| 2004/0260206 A1 | | 12/2004 | Murayama et al. |
| 2005/0027339 A1 | * | 2/2005 | Schrom .................... A61N 1/05 607/116 |
| 2006/0074318 A1 | | 4/2006 | Ahmed et al. |
| 2007/0219551 A1 | | 9/2007 | Honour et al. |
| 2007/0250036 A1 | | 10/2007 | Volk et al. |
| 2007/0255514 A1 | | 11/2007 | Smith |
| 2010/0114278 A1 | * | 5/2010 | McMorrow .......... A61N 1/0553 607/116 |
| 2010/0318019 A1 | * | 12/2010 | Nee .................... A61M 25/0012 604/21 |
| 2012/0130220 A1 | | 5/2012 | Maskara et al. |
| 2014/0180141 A1 | | 6/2014 | Millett |
| 2014/0187980 A1 | | 7/2014 | Burkett |
| 2014/0187984 A1 | | 7/2014 | Burkett |

FOREIGN PATENT DOCUMENTS

| | | |
|---|---|---|
| JP | 2007296354 A | 11/2007 |
| WO | WO 2006/050385 | 5/2006 |
| WO | WO 2012/173697 | 12/2012 |

OTHER PUBLICATIONS

International Searching Authority/European Patent Office, "Communication—Partial Supplementary European Search Report," for European Application No. 13866830.6, dated Jul. 12, 2016, 7 pages.
International Searching Authority/European Patent Office, "Communication—Extended European Search Report," for European Application No. 13866830.6, dated Oct. 14, 2016, 12 pages.

* cited by examiner

INTRAVASCULAR DEVICES, SYSTEMS, AND METHODS

CROSS-REFERENCE TO RELATED APPLICATIONS

The present application claims priority to and the benefit of U.S. Provisional Patent Application No. 61/747,578, filed Dec. 31, 2012 and U.S. Provisional Patent Application No. 61/777,516, filed Mar. 12, 2013, each of which is hereby incorporated by reference in its entirety.

TECHNICAL FIELD

The present disclosure relates to intravascular devices, systems, and methods. In some embodiments, the intravascular devices are guidewires that include one or more electronic, optical, or electro-optical components.

BACKGROUND

Heart disease is very serious and often requires emergency operations to save lives. A main cause of heart disease is the accumulation of plaque inside the blood vessels, which eventually occludes the blood vessels. Common treatment options available to open up the occluded vessel include balloon angioplasty, rotational atherectomy, and intravascular stents. Traditionally, surgeons have relied on X-ray fluoroscopic images that are planar images showing the external shape of the silhouette of the lumen of blood vessels to guide treatment. Unfortunately, with X-ray fluoroscopic images, there is a great deal of uncertainty about the exact extent and orientation of the stenosis responsible for the occlusion, making it difficult to find the exact location of the stenosis. In addition, though it is known that restenosis can occur at the same place, it is difficult to check the condition inside the vessels after surgery with X-ray.

A currently accepted technique for assessing the severity of a stenosis in a blood vessel, including ischemia causing lesions, is fractional flow reserve (FFR). FFR is a calculation of the ratio of a distal pressure measurement (taken on the distal side of the stenosis) relative to a proximal pressure measurement (taken on the proximal side of the stenosis). FFR provides an index of stenosis severity that allows determination as to whether the blockage limits blood flow within the vessel to an extent that treatment is required. The normal value of FFR in a healthy vessel is 1.00, while values less than about 0.80 are generally deemed significant and require treatment.

Often intravascular catheters and guidewires are utilized to measure the pressure within the blood vessel, visualize the inner lumen of the blood vessel, and/or otherwise obtain data related to the blood vessel. To date, guidewires containing pressure sensors, imaging elements, and/or other electronic, optical, or electro-optical components have suffered from reduced performance characteristics compared to standard guidewires that do not contain such components. For example, the handling performance of previous guidewires containing electronic components have been hampered, in some instances, by the limited space available for the core wire after accounting for the space needed for the conductors or communication lines of the electronic component(s), the stiffness of the rigid housing containing the electronic component(s), and/or other limitations associated with providing the functionality of the electronic components in the limited space available within a guidewire. Further, due to its small diameter, in many instances the proximal connector portion of the guidewire (i.e., the connector(s) that facilitate communication between the electronic component(s) of the guidewire and an associated controller or processor) is fragile and prone to kinking, which can destroy the functionality of the guidewire. For this reason, surgeons are reluctant to remove the proximal connector from the guidewire during a procedure for fear of breaking the guidewire when reattaching the proximal connector. Having the guidewire coupled to the proximal connector further limits the maneuverability and handling of the guidewire.

Further, a problem with existing pressure and flow guidewires is that they require a complex assembly of many discrete components. That complex assembly process has limitations on design performance of the guidewire. The use of separate conductive wires running down the length of the wire reduces the space available for more frontline supportive cores and can result in numerous issues during use due to poor solder joints with conductive bands, electrical shorts due to insulation issues, and breakage of the delicate conductive wires.

Accordingly, there remains a need for improved intravascular devices, systems, and methods that include one or more electronic, optical, or electro-optical components.

SUMMARY

The present disclosure is directed to intravascular devices, systems, and methods that include a guide wire having a solid core wire with electrical conductors formed or wrapped thereon.

The invention provides a more robust sensing guidewire that avoids the assembly and performance issues of prior art sensing guidewires. Guidewires of the invention have a core wire that is coated with an outer layer. Conductive wires are embedded in the outer layer and run the length of the body. The conductive wires act as the electrical pathway for sensor signals. The outer layer is removed (e.g., by ablation) at specific locations on each conductive wire where electrical connections are required. A conductive material is then applied to the exposed sections of wire. The sensor may then be coupled to the guidewire via the conductive material at one or more of the exposed sections. In this manner, guidewires of the invention eliminate the need to assemble a multitude of components to create the conductive band connections, the need for a hypotube, and the use of adhesives and solder in the guidewire. Reducing the number of components to assemble guidewires of the invention improves robustness of the assembled wire by eliminating a multitude of processes that can create failure conditions. Additionally, the ability to print the conductive bands eliminates the complexity associated with having to run and connect multiple wires.

Any type of sensor can be connected to guidewires of the invention and the type of measurement will determine the type of sensor used. In certain embodiments, only a single sensor is connected to the guidewire. In other embodiments, multiple sensors are connected to the guidewire. All of the sensors may be the same. Alternatively, the sensors may differ from each other and measure different characteristics inside a vessel. Exemplary sensors are pressure, flow, and temperature sensors. Any type of pressure sensor may be used with guidewires of the invention. In certain embodiments, the pressure sensor includes a crystalline semiconductor material. Any type of flow sensor may be used with guidewires of the invention. In certain embodiments, the flow sensor includes an ultrasound transducer.

Preferably, the guidewire of the invention includes both a pressure sensor and a flow sensor on the distal portion. Pressure sensors are able to obtain pressure measurements and flow sensors are able to obtain blood velocity measurements within a blood vessel. The ability to measure and compare both the pressure and velocity flow significantly improves the diagnostic accuracy of ischemic testing.

Numerous different methods exist to apply the conductive material to the exposed sections on the body. In certain embodiments, printing is used and the conductive material is a conductive ink. Typically, the conductive ink includes a conductive metal, such as gold. The remainder of the outer layer in which the conductive wires are embedded is typically a polymeric material, such as polyimide.

Another aspect of the invention provides a method for measuring a characteristic inside a vessel. Methods of the invention involve providing a sensing guidewire that includes a body having an inner core and an outer layer. One or more conductive wires are embedded in the outer layer. The conductive wires are exposed at one or more locations along the body. A conductive material is layered over a plurality of the exposed locations, and a sensor is coupled to the body via the conductive material at one of the exposed locations. The guidewire is inserted into a vessel, and one or more sensors on the guidewire measure one or more characteristics inside the vessel.

In some embodiments, a guide wire having a solid core wire with electrical conductors printed thereon is provided. In some instances, the electrical conductors are formed by defining a helically wrapped pattern around the solid core wire. The pattern may be defined with wire, by printing conductive ink, by isolating a conductive skin or surface via laser ablation into multiple conductive surfaces, by the LDS-MID process, etc. The number of electrical conductors is dependent upon the functionality of the device, but in some implementations includes between two and six conductors. In some implementations, the solid core wire operates as an electrical conductor of the guide wire. In some instances, one or more conductive bands are coupled to the electrical conductors adjacent a proximal portion of the guide wire. In some instances, the conductive bands are soldered, welded, or glued (with a conductive adhesive) to the electrical conductors. In some embodiments, the conductive bands are printed over an exposed portion of a corresponding conductor—another is swaged. In some instances printed pattern is an antenna(s), heating element (s), tactile surface(s), alpha-numeric characters, etc.

In some instances, methods of assembling and/or manufacturing the guide wires disclosed herein are provided. In some embodiments, the traditional need to manually solder loose 48 AWG insulated wires to 0.35 nm cylindrical conductive bands is eliminated, which increases manufacturing yields and reduces the necessary training and skill required for operators. Further, instead of relying upon a single solder connection, the conductive bands of the present disclosure are electrically coupled to an associated conductor along a majority of the length of the conductive band. Also, in some instances the number of parts needed to manufacture at least the proximal connector portion of the device is reduced.

The present disclosure enables the proximal connector region of a guide wire that is stronger and more durable than existing designs, while also easier to manufacture. Embodiments of the present disclosure utilize precision material deposition (e.g., to coat and/or trace precision patterns) and/or wire winding(s) with a solid core member facilitating the use of a larger core that provides better handling, strength, and durability than existing designs, which reduces the likelihood of unwanted bending, kinking, and/or other damage to the proximal connector portion of the intravascular device that can be detrimental to the function of the device.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which:

Collectively.

FIG. 2 is a diagrammatic perspective view of a core member according to an embodiment of the present disclosure.

FIG. 3 is a close-up diagrammatic perspective view of a proximal end of the core member of FIG. 2.

FIG. 4 is a diagrammatic perspective view of the core member of FIGS. 2 and 3 after application of an insulating layer to a section of the core member according to an embodiment of the present disclosure.

FIG. 5 is a diagrammatic perspective view of the core member of FIGS. 2-4 with a four conductors helically wrapped around the core member according to an embodiment of the present disclosure.

FIG. 6 is a close-up diagrammatic perspective view of a proximal section of the core member, showing portions of two of the helically-wrapped conductors.

FIG. 7 is a close-up diagrammatic perspective view of a proximal section of the core member showing an exposed portion of the first conductor and portions of the second, third, and fourth conductors covered in an insulating material.

FIG. 8 is a close-up diagrammatic perspective view of a proximal section of the core member similar to that of FIG. 7, but showing an exposed portion of the second conductor and portions of the third and fourth conductors covered in an insulating material.

FIG. 9 is a close-up diagrammatic perspective view of a proximal section of the core member similar to those of FIGS. 7 and 8, but showing an exposed portion of the third conductor and a portion of the fourth conductor covered in an insulating material.

FIG. 10 is a diagrammatic perspective view of the core member of FIGS. 2-9 with four conductive bands positioned around the core member according to an embodiment of the present disclosure.

FIG. 11 is a close-up diagrammatic perspective view of a proximal section of the core member showing a spacing between portions of two adjacent conductive bands.

FIG. 12 is a close-up diagrammatic perspective view of the proximal section of the core member of FIG. 11 after the spacing between the two adjacent conductive bands is filled with an insulating material.

FIG. 13 is a diagrammatic perspective view of the core member of FIGS. 2-12 after the spacings between each of the conductive bands has been filled with an insulating material.

DETAILED DESCRIPTION

Figure 1:
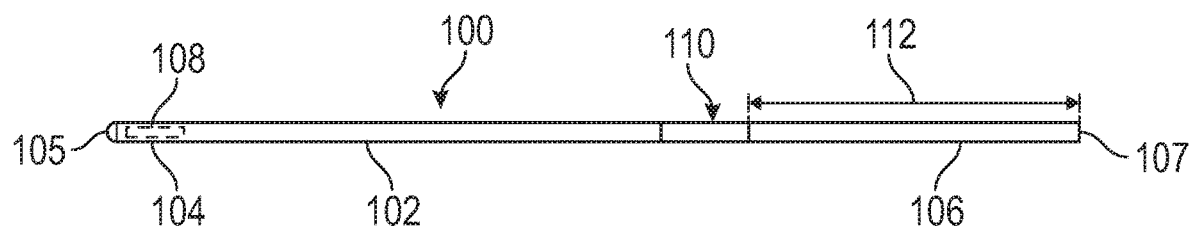
FIG. 1 is a diagrammatic, schematic side view of an intravascular device according to an embodiment of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

As used herein, "flexible elongate member" or "elongate flexible member" includes at least any thin, long, flexible structure that can be inserted into the vasculature of a patient. While the illustrated embodiments of the "flexible elongate members" of the present disclosure have a cylindrical profile with a circular cross-sectional profile that defines an outer diameter of the flexible elongate member, in other instances all or a portion of the flexible elongate members may have other geometric cross-sectional profiles (e.g., oval, rectangular, square, elliptical, etc.) or non-geometric cross-sectional profiles. Flexible elongate members include, for example, guidewires and catheters. In that regard, catheters may or may not include a lumen extending along its length for receiving and/or guiding other instruments. If the catheter includes a lumen, the lumen may be centered or offset with respect to the cross-sectional profile of the device.

In most embodiments, the flexible elongate members of the present disclosure include one or more electronic, optical, or electro-optical components. For example, without limitation, a flexible elongate member may include one or more of the following types of components: a pressure sensor, a temperature sensor, an imaging element, an optical fiber, an ultrasound transducer, a reflector, a mirror, a prism, an ablation element, an RF electrode, a conductor, and/or combinations thereof. Generally, these components are configured to obtain data related to a vessel or other portion of the anatomy in which the flexible elongate member is disposed. Often the components are also configured to communicate the data to an external device for processing and/or display. In some aspects, embodiments of the present disclosure include imaging devices for imaging within the lumen of a vessel, including both medical and non-medical applications. However, some embodiments of the present disclosure are particularly suited for use in the context of human vasculature. Imaging of the intravascular space, particularly the interior walls of human vasculature can be accomplished by a number of different techniques, including ultrasound (often referred to as intravascular ultrasound ("IVUS") and intracardiac echocardiography ("ICE")) and optical coherence tomography ("OCT"). In other instances, infrared, thermal, or other imaging modalities are utilized.

The electronic, optical, and/or electro-optical components of the present disclosure are often disposed within a distal portion of the flexible elongate member. As used herein, "distal portion" of the flexible elongate member includes any portion of the flexible elongate member from the mid-point to the distal tip. As flexible elongate members can be solid, some embodiments of the present disclosure will include a housing portion at the distal portion for receiving the electronic components. Such housing portions can be tubular structures attached to the distal portion of the elongate member. Some flexible elongate members are tubular and have one or more lumens in which the electronic components can be positioned within the distal portion.

The electronic, optical, and/or electro-optical components and the associated communication lines are sized and shaped to allow for the diameter of the flexible elongate member to be very small. For example, the outside diameter of the elongate member, such as a guidewire or catheter, containing one or more electronic, optical, and/or electro-optical components as described herein are between about 0.0007" (0.0178 mm) and about 0.118" (3.0 mm), with some particular embodiments having outer diameters of approximately 0.014" (0.3556 mm) and approximately 0.018" (0.4572 mm)). As such, the flexible elongate members incorporating the electronic, optical, and/or electro-optical component(s) of the present application are suitable for use in a wide variety of lumens within a human patient besides those that are part or immediately surround the heart, including veins and arteries of the extremities, renal arteries, blood vessels in and around the brain, and other lumens.

"Connected" and variations thereof as used herein includes direct connections, such as being glued or otherwise fastened directly to, on, within, etc. another element, as well as indirect connections where one or more elements are disposed between the connected elements.

"Secured" and variations thereof as used herein includes methods by which an element is directly secured to another element, such as being glued or otherwise fastened directly to, on, within, etc. another element, as well as indirect techniques of securing two elements together where one or more elements are disposed between the secured elements.

Referring now to FIG. 1, shown therein is a portion of an intravascular device 100 according to an embodiment of the present disclosure. In that regard, the intravascular device 100 includes a flexible elongate member 102 having a distal portion 104 adjacent a distal end 105 and a proximal portion 106 adjacent a proximal end 107. A component 108 is positioned within the distal portion 104 of the flexible elongate member 102 proximal of the distal tip 105. Generally, the component 108 is representative of one or more electronic, optical, or electro-optical components. In that regard, the component 108 is a pressure sensor, a temperature sensor, an imaging element, an optical fiber, an ultrasound transducer, a reflector, a mirror, a prism, an ablation element, an RF electrode, a conductor, and/or combinations thereof. The specific type of component or combination of components can be selected based on an intended use of the intravascular device. In some instances, the component 108 is positioned less than 10 cm, less than 5, or less than 3 cm from the distal tip 105. In some instances, the component 108 is positioned within a housing of the flexible elongate member 102. In that regard, the housing is a separate component secured to the flexible elongate member 102 in some instances. In other instances, the housing is integrally formed as a part of the flexible elongate member 102.

The intravascular device 100 also includes a connector 110 adjacent the proximal portion 106 of the device. In that regard, the connector 110 is spaced from the proximal end 107 of the flexible elongate member 102 by a distance 112. Generally, the distance 112 is between 0% and 50% of the total length of the flexible elongate member 102. While the total length of the flexible elongate member can be any length, in some embodiments the total length is between about 1300 mm and about 4000 mm, with some specific embodiments have a length of 1400 mm, 1900 mm, and 3000 mm. Accordingly, in some instances the connector 110 is positioned at the proximal end 107. In other instances, the connector 110 is spaced from the proximal end 107. For example, in some instances the connector 110 is spaced from the proximal end 107 between about 0 mm and about 1400 mm. In some specific embodiments, the connector 110 is spaced from the proximal end by a distance of 0 mm, 300 mm, and 1400 mm.

The connector 110 is configured to facilitate communication between the intravascular device 100 and another device. More specifically, in some embodiments the connector 110 is configured to facilitate communication of data obtained by the component 108 to another device, such as a computing device or processor. Accordingly, in some embodiments the connector 110 is an electrical connector. In such instances, the connector 110 provides an electrical connection to one or more electrical conductors that extend along the length of the flexible elongate member 102 and are electrically coupled to the component 108. Some specific embodiments of electrical connectors in accordance with the present disclosure are discussed below in the context of FIGS. 5-11. In other embodiments, the connector 110 is an optical connector. In such instances, the connector 110 provides an optical connection to one or more optical communication pathways (e.g., fiber optic cable) that extend along the length of the flexible elongate member 102 and are optically coupled to the component 108. Further, in some embodiments the connector 110 provides both electrical and optical connections to both electrical conductor(s) and optical communication pathway(s) coupled to the component 108. In that regard, it should again be noted that component 108 is comprised of a plurality of elements in some instances. In some instances, the connector 110 is configured to provide a physical connection to another device, either directly or indirectly. In other instances, the connector 110 is configured to facilitate wireless communication between the intravascular device 100 and another device. Generally, any current or future developed wireless protocol(s) may be utilized. In yet other instances, the connector 110 facilitates both physical and wireless connection to another device.

As noted above, in some instances the connector 110 provides a connection between the component 108 of the intravascular device 100 and an external device. Accordingly, in some embodiments one or more electrical conductors, one or more optical pathways, and/or combinations thereof extend along the length of the flexible elongate member 102 between the connector 110 and the component 108 to facilitate communication between the connector 110 and the component 108. Generally, any number of electrical conductors, optical pathways, and/or combinations thereof can extend along the length of the flexible elongate member 102 between the connector 110 and the component 108. In some instances, between one and ten electrical conductors and/or optical pathways extend along the length of the flexible elongate member 102 between the connector 110 and the component 108. The number of communication pathways and the number of electrical conductors and optical pathways extending along the length of the flexible elongate member 102 is determined by the desired functionality of the component 108 and the corresponding elements that define component 108 to provide such functionality.

Referring now to FIGS. 2-13, shown therein are aspects of assembling and/or manufacturing intravascular devices of the present disclosure that include communication pathways (e.g., electrical conductors and/or optical fibers) extending along the length of the device. In that regard, one of the major issues associated with existing functional guidewires is poor mechanical performance as compared to frontline guidewires. This performance loss is due in a large part to the typical design of the guidewires that severely limits the space available for the core or core wire due to the need to run the communication lines along the length of the device between the core wire and a surrounding hypotube. For the sake of clarity and simplicity, the embodiments of FIGS. 2-13 include four electrical conductors in addition to an electrically conductive core. Those skilled in the art will recognize that the concepts are applicable to intravascular devices that include virtually any number of electrical conductors and/or optical fibers extending along the length of the core wire. However, in most implementations the intravascular device will include between 1 and 10 communication pathways extending along the length of the core wire between a proximal portion and a distal portion of the intravascular device.

Figure 2:
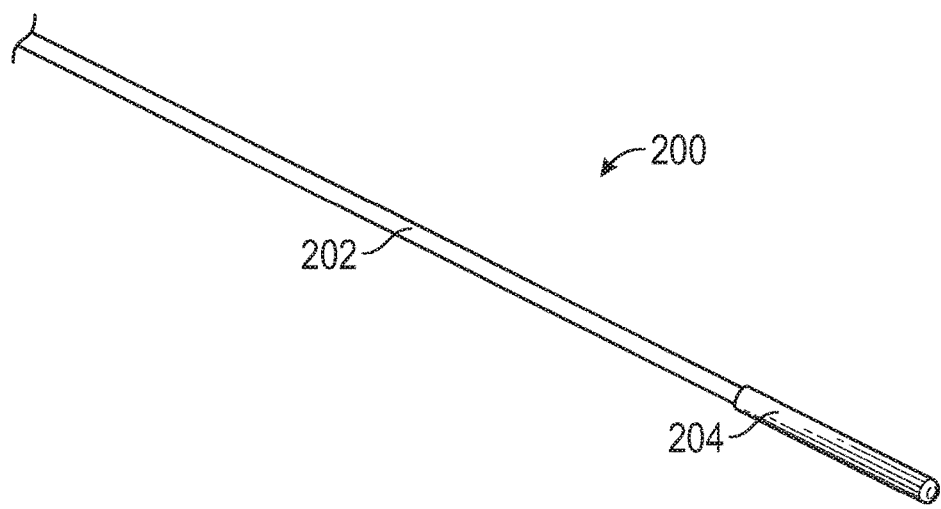
FIGS. 2-13 illustrate aspects of manufacturing an intravascular device according to an embodiment of the present disclosure.
Figure 3:
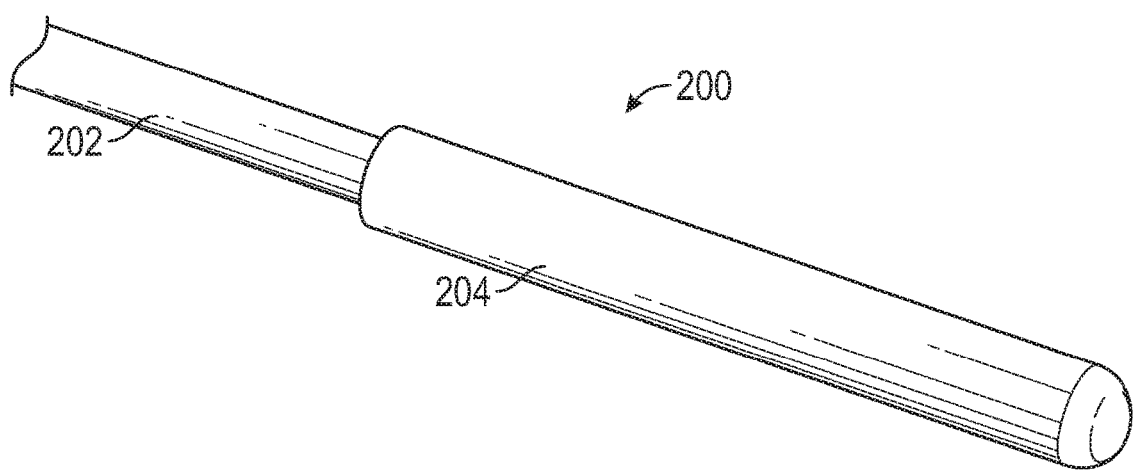

Referring more specifically to FIG. 2, shown therein is a diagrammatic perspective view of a core member 200 according to an embodiment of the present disclosure. As shown, the core member 200 includes an elongated shaft 202 and connector 204. In the illustrated embodiment, the connector 204 has an increased diameter with respect to the shaft 202. In some instances, the outer diameter of the connector 204 is the same as the desired outer diameter of the intravascular device that the core member 200 is intended to form. Accordingly, in some particular embodiments the outer diameter of the connector 204 is approximately 0.014". The difference in diameters between the shaft 202 and the connector 204 may result from removing material away from a constant diameter rod to define the shaft and/or adding material to a constant diameter rod to define the connector. In some instances, the connector 204 is defined by a conductive band (such as those described below for the other conductors of the intravascular device) that is electrically coupled to the core member. In that regard, the core member 200 is formed of a conductive material (or at least plated with a conductive material) in some instances. In some instances, the core member 200 carries the common or ground signal for the components of the intravascular device. As shown in FIG. 3, the connector 204 defines the proximal most connector of the intravascular device and, in the illustrated embodiment, is positioned at the proximal tip of the intravascular device. In that regard, the proximal tip of the connector 204 is rounded. In some implementations, the proximal most connector is spaced distally from the proximal tip of the intravascular device.

Figure 4:
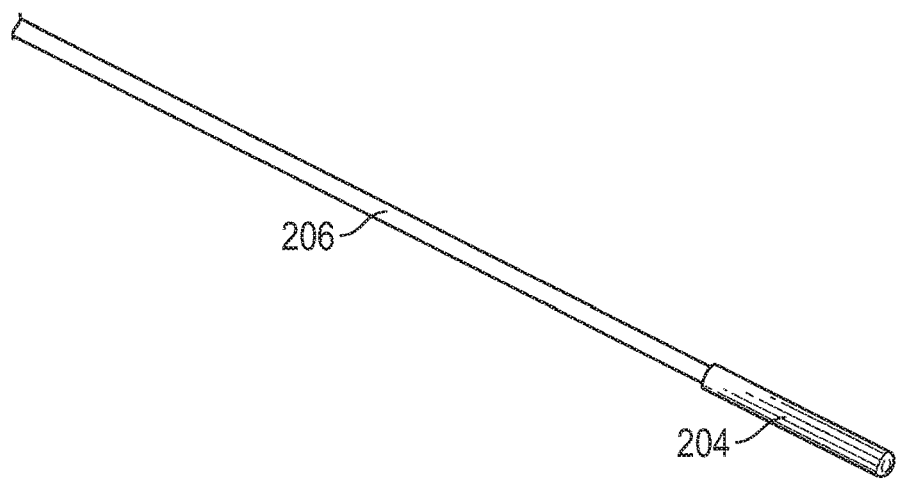

Referring now to FIG. 4, shown therein is a diagrammatic perspective view of the core member 200 after application of an insulating layer 206 to the shaft 202 of the core member. In that regard, the insulating layer 206 serves to electrically isolate the conductive core member 200 from the conductors that will be subsequently applied over the shaft 202. The insulating layer 206 may be formed of any suitable material. In some implementations, the insulating layer 206 is a parylene layer. Other elements may also be formed over, placed onto, and/or connected to shaft 202 in some instances, including flex-foil wrap conductors, conductive bands, pads, circuits, dielectrics, and/or other components of the intravascular device.

Figure 5:
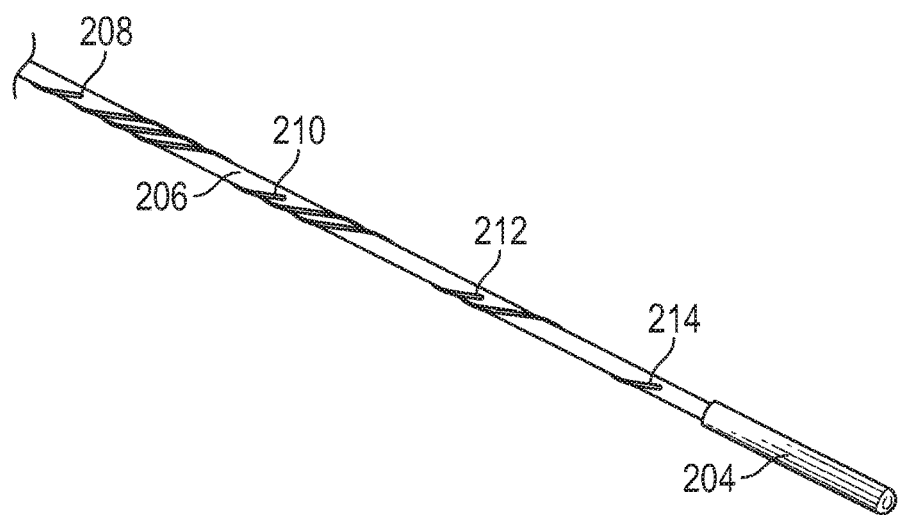
Figure 6:
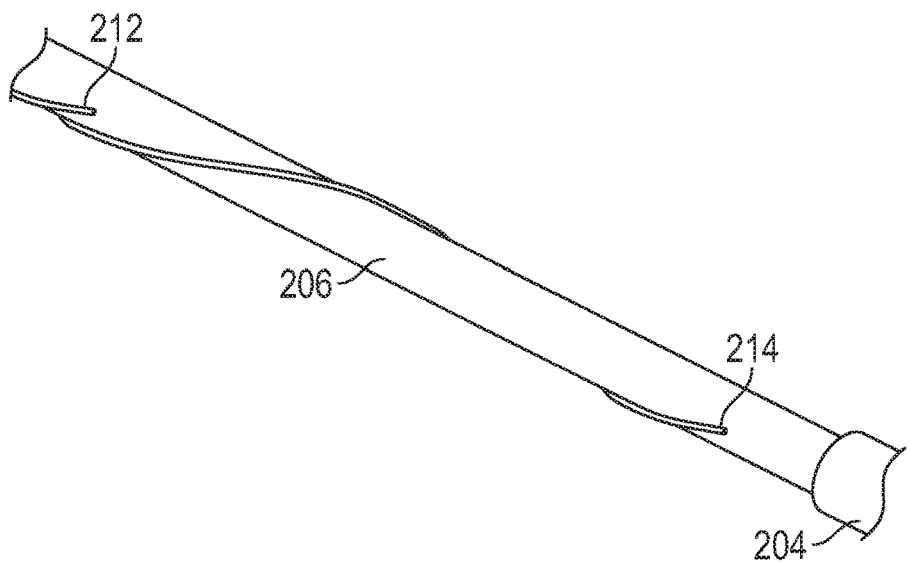

Referring now to FIG. 5, shown therein is a diagrammatic perspective view of the core member 200 with four conductors 208, 210, 212, and 214 helically wrapped around the shaft 202 of the core member (may also be conductive). As shown the proximal ends of the conductors 208, 210, 212, and 214 are spaced apart along the length of the core member. In some instances, the spacing between the ends of the conductors corresponds to a desired spacing between conductive bands that will be coupled to the conductors 208, 210, 212, and 214. The conductors 208, 210, 212, and 214 may be formed by electrically printing (micro-dispense, aero-jet, ink-jet, transfer, gravure, etc.) or plating of a conductive material over the insulating layer in a desired pattern. In some instances, a conductive ink is utilized. In other instances, 48 AWG or smaller conductors are helically wrapped around the shaft 202. In such instances, the conductors may be insulated or not. In that regard, the conductors may be wire (Cu, etc.), carbon nanotube fiber conductors, conductive ink, conductive polymer, conductive film, and/or combinations thereof. If the conductors are not insulated, then they are kept isolated (i.e., spaced) from one another as shown in FIG. 5. FIG. 6 provides a close-up diagrammatic perspective view of a proximal section of the core member 200, showing proximal end portions of helically-wrapped conductors 212 and 214.

In other embodiments, the conductors and/or other elements of the intravascular device are secured and/or wrapped around the core member using other techniques, including without limitation flex-foil wrapping, roll-to-roll printing, singulation, wrapping tape with conductors, utilizing conductive bands, utilizing contact pads, and/or utilizing other features. For example, in some instances a flex-foil wrap is utilized to define at least a portion of the conductors and/or circuitry. In that regard, insulated flexible foil conductors are helically wound onto the core member in some instances. The flexible foil conductors may define one or more conductors and/or circuitry such that a single foil conductor (having a multiple conductive leads/traces/circuits) and/or multiple foil conductors (each having single or multiple conductive leads/traces/circuits) may be utilized. Flexible foil conductors allow for a precise and consistent outer diameter, length, and pitch of the conductors around the core member, including facilitating automatic processing techniques. As a result, the resulting device can have improved consistency with respect to straightness and flexibility. As another example, in some instances a mill and fill approach is utilized to define the conductors around the core member.

Figure 7:
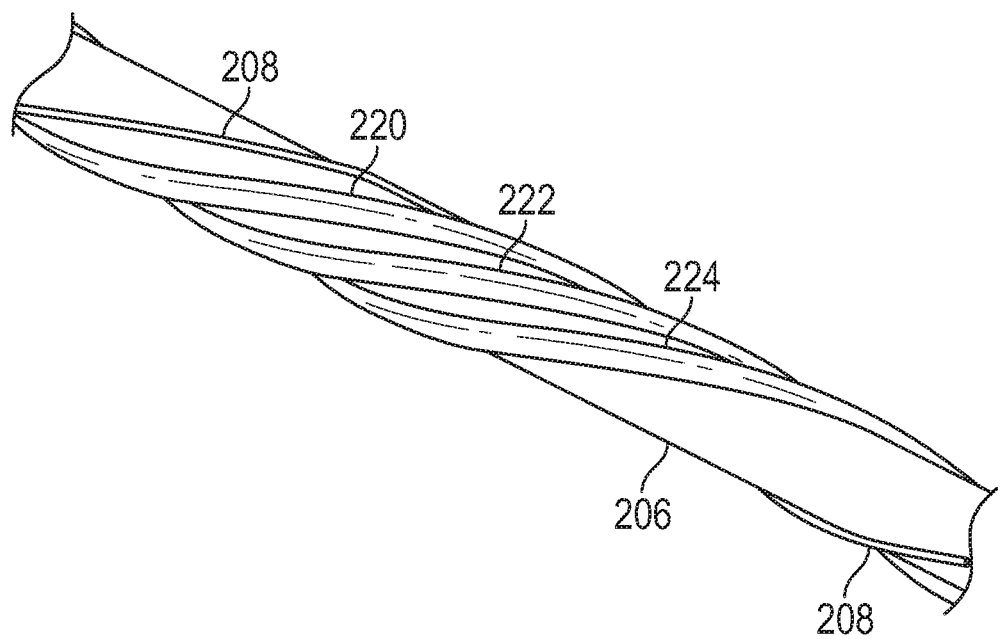
Figure 8:
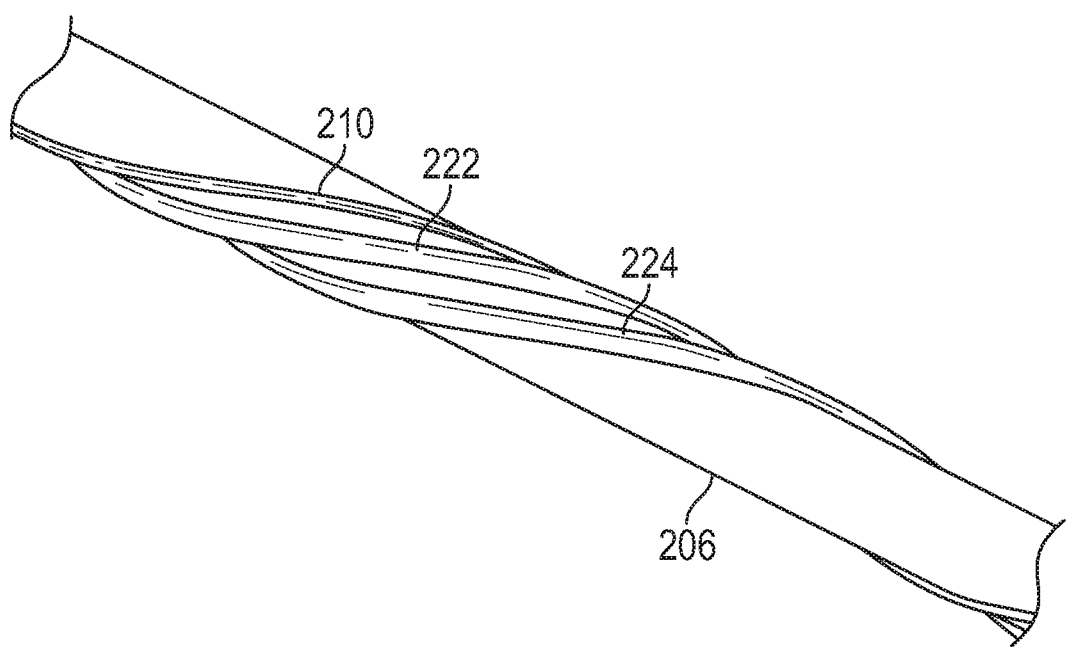
Figure 9:
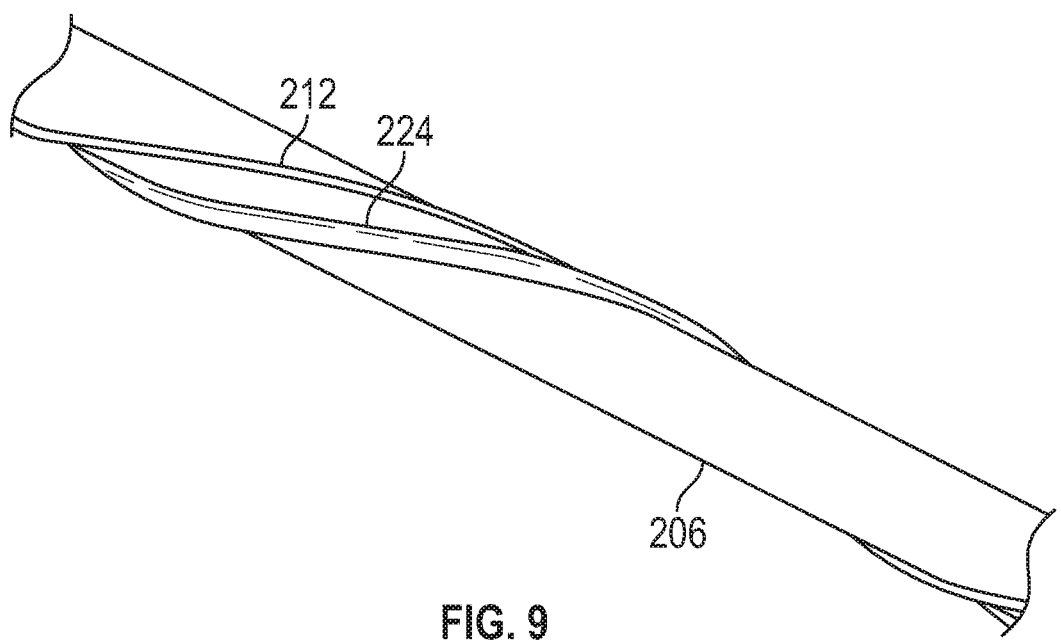

Referring now to FIG. 7, shown therein is a close-up diagrammatic perspective view of a proximal section of the core member showing an exposed portion of conductor 208 and portions of conductors 210, 212, and 214 that have been covered in an insulating material and designated as 220, 222, and 224, respectively. In that regard, after the conductors 208, 210, 212, and 214 have been formed/wrapped around the shaft 202, an insulating layer is formed over all or a majority of the length of the conductors. By either masking a section of each conductor and/or subsequently removing the applied (or existing) insulating layer, a section of each conductor 208, 210, 212, and 214 is exposed. Conductive bands are coupled to the exposed sections the conductors 208, 210, 212, and 214 as discussed below in order to define the proximal connector portion of the intravascular device. In this regard, FIG. 8 is a close-up diagrammatic perspective view of a proximal section of the core member 200 showing an exposed portion of conductor 210 and the insulated portions 222 and 224 of conductors 212 and 214. Similarly, FIG. 9 is a close-up diagrammatic perspective view of a proximal section of the core member 200 showing an exposed portion of conductor 212 and the insulated portion 224 of conductor 214.

Figure 10:
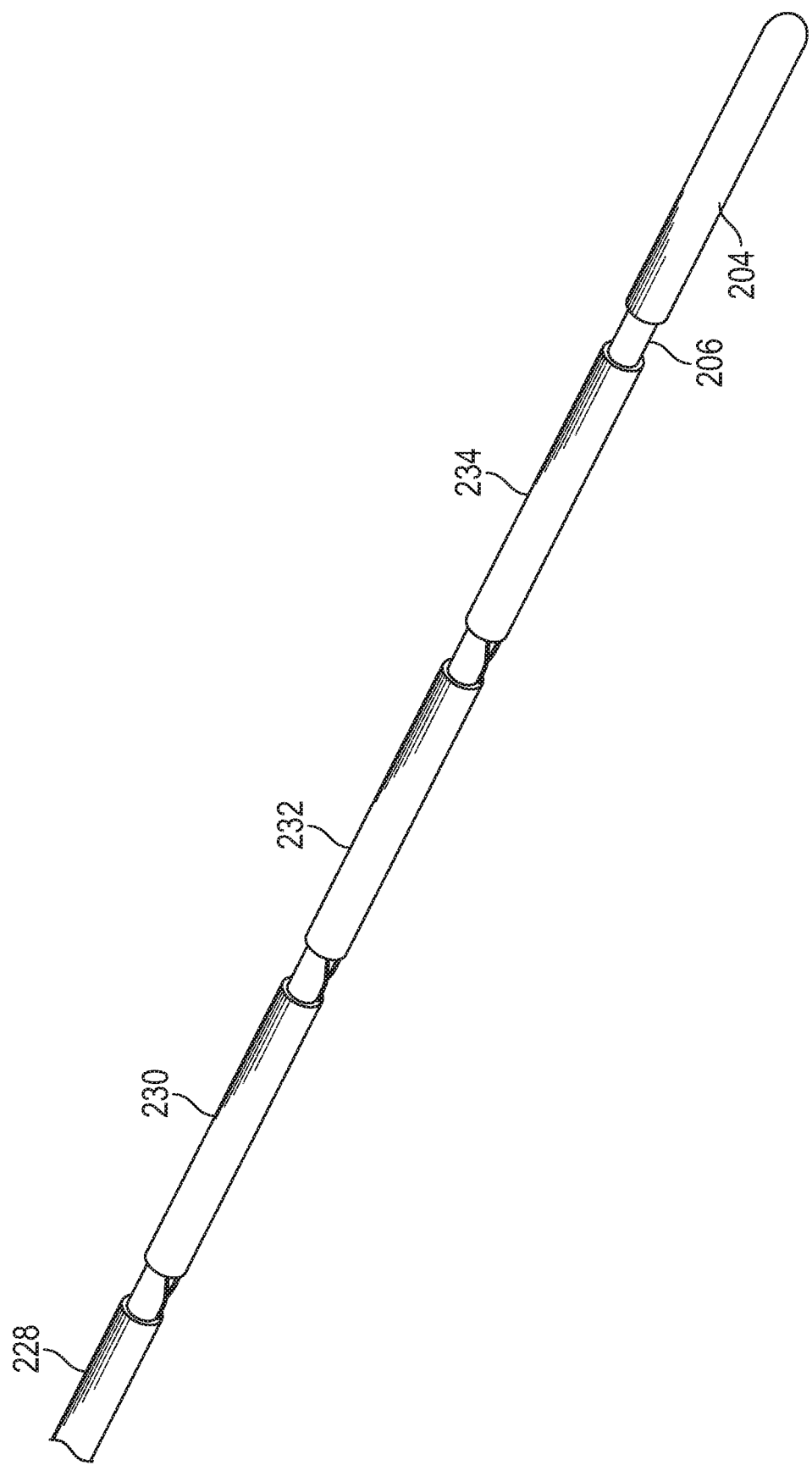
Figure 11:
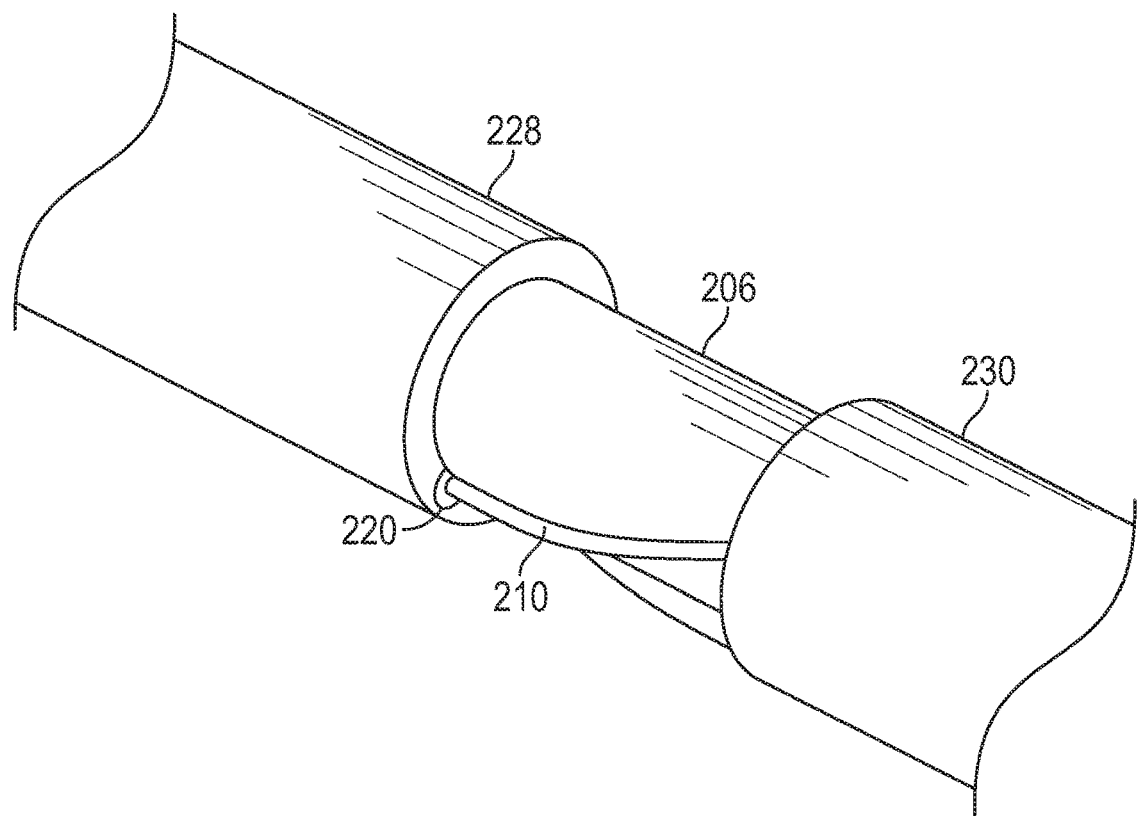

Referring now to FIG. 10, shown therein is a diagrammatic perspective view of the core member 200 with five conductive bands 228, 230, 232, 234, and 204 positioned around and/or defined by the core member in alignment with the exposed portions of the conductors 208, 210, 212, 214, and 202 according to an embodiment of the present disclosure. In some instances, the conductive bands 228, 230, 232, and 234 are printed onto the shaft 202 of the core member 200 by electrically printing or plating of a conductive material over the exposed portions of the conductors 208, 210, 212, and 214. In that regard, the conductive bands 228, 230, 232, and 234 are formed such that they have a uniform outer diameter matching the desired outer diameter of the intravascular device and/or the outer diameter of connector 204 in some implementations. In some instances, the conductive bands are preformed cylindrical members that are positioned over the corresponding exposed sections of the conductors 208, 210, 212, and 214 and electrically coupled to the conductors using solder or other suitable techniques. FIG. 11 provides a close-up diagrammatic perspective view of a proximal section of the core member showing a spacing between adjacent conductive bands 228 and 230. Also shown in FIG. 11 is how the conductive band 228 is formed around, and electrically connected to conductor 208, while forming around the insulated portions 206, 220, 222, 224 of core member 202, conductors 210, 212, and 214 respectively. In the illustrated embodiment, the insulated portion 220 and the end of conductive band 228 are substantially aligned along the length of the core member 200, but in other embodiments the insulated portion 220 extends proximally towards conductive band 230 (including into a portion of the interior of conductive band 230, in some instances) to ensure the conductor 210 is isolated from the conductor 208 and conductive band 228.

In some embodiments, the conductive bands are swaged and/or laser welded in place. In that regard, as a general manufacturing process swaging may be broken up into two categories. The first category of swaging involves the work piece being forced through a confining die to reduce its diameter, similar to the process of drawing wire. This may also be referred to as "tube swaging." The second category involves two or more dies used to hammer a round workpiece into a smaller diameter. This process is usually called "rotary swaging" or "radial forging." Tubes may be tagged (reduced in diameter to enable the tube to be initially fed through the die to then be pulled from the other side) using a rotary swager, which allows them to be drawn on a draw bench. Swaging is often the method of choice for precious metals since there is no loss of material in the process. In that regard, in some instances the conductive band is swaged around the core member and a portion of the conductive band is laser-welded to the exposed conductor underneath the conductive band.

Figure 12:
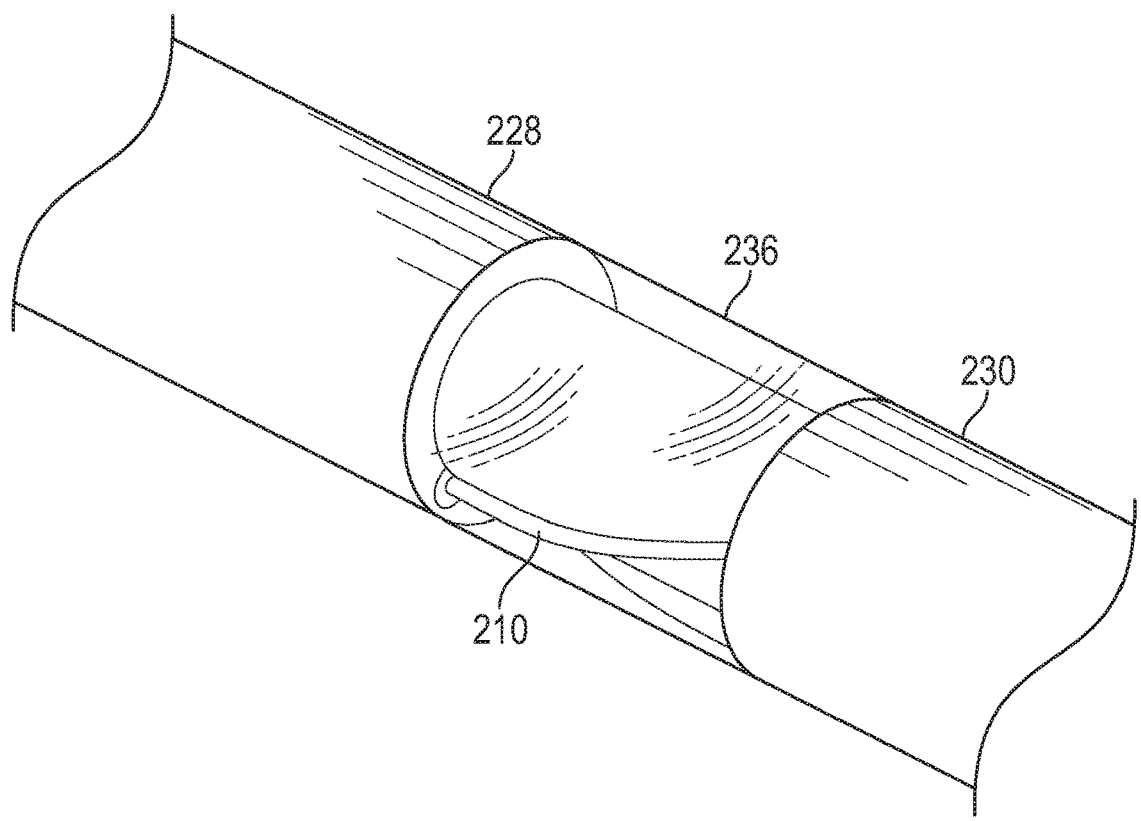
Figure 13:
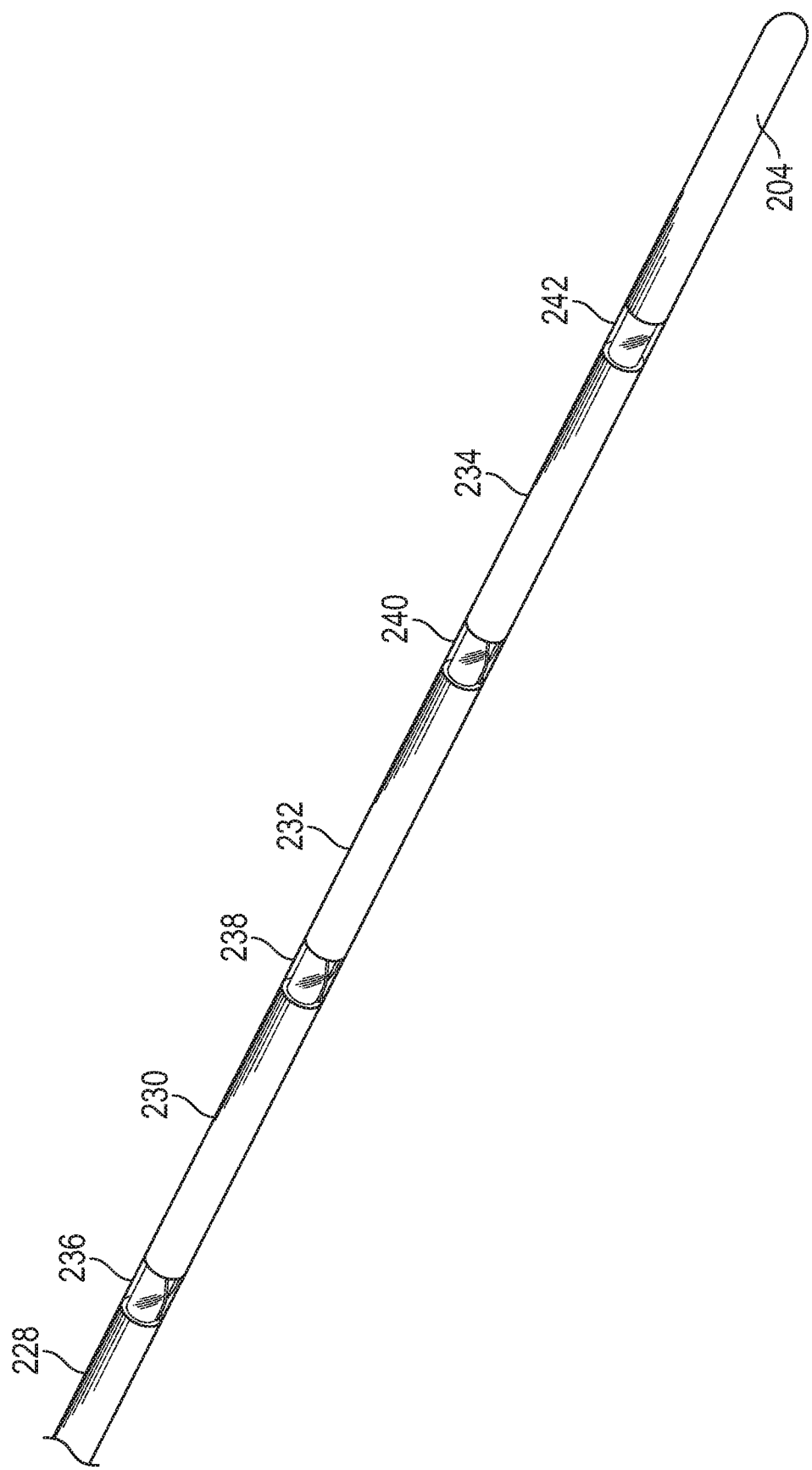

Referring now to FIG. 12, shown therein is a close-up diagrammatic perspective view of the proximal section of the core member of FIG. 11 after the spacing between the adjacent conductive bands 228 and 230 is filled with an insulating material 236. Similarly, FIG. 13 provides a diagrammatic perspective view of the core member 200 after the spacings between each of the conductive bands has been filled with an insulating material, defining insulating spacers 236, 238, 240, and 242. The insulating spacers 236, 238, 240, and 242 are formed such that they have a uniform outer diameter matching the desired outer diameter of the intravascular device and/or the outer diameters of conductive bands 204, 228, 230, 232, and 234 in some implementations. The insulating material utilized to form insulating spacers 236, 238, 240, and 242 may be any suitable insulating material.

Figure 14:
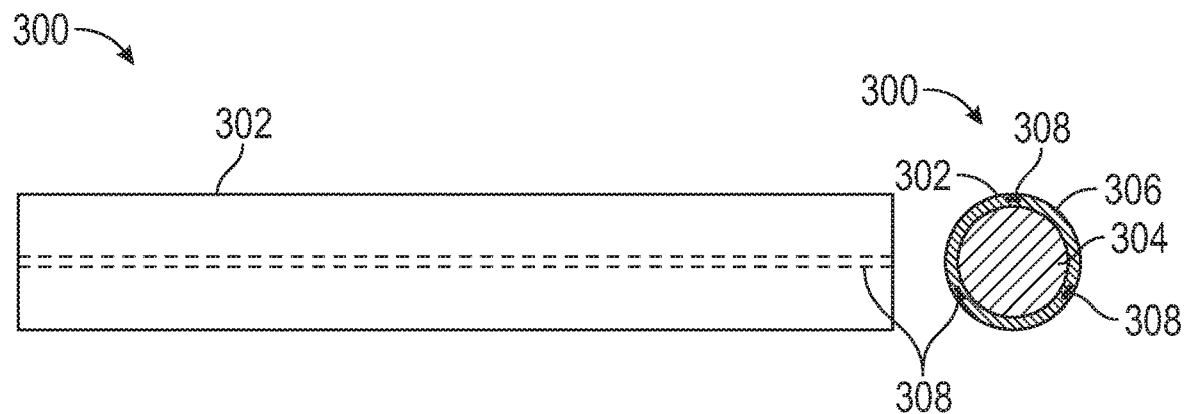
FIG. 14 shows show an exemplary embodiment of a body with conductive wires impregnated therein. The image on the left is a side view and the image of the right is a cross-sectional view.

FIG. 14 shows an exemplary embodiment of a portion of an intravascular device 300 comprising a flexible elongate member 302 that includes a core member 304 surrounded ty an outer layer 306 with conductive wires 308 impregnated therein. Both a side view and a cross-sectional end view of the flexible elongate member 302 are provided. The core member 304 can be formed of a suitable material such as stainless steel, nickel and titanium alloy (Nitinol), polyetheretherketone, heat straightened 304 stainless steel, or other metallic or polymeric materials, using techniques well known in the art. The outer layer 306 can be formed of a suitable polymeric material. In that regard, the outer layer 306 is coated onto the wire using standard wire coating techniques. As the thickness of the coating is built up, conductive wires 308 are introduced into the coating process such that they become completely coated in the outer layer 306. The outer layer 406 may be any polymeric material, and a preferred material is polyimide. In certain embodiments, the conductive wires 308 are space substantially equally around a diameter of the body. In certain embodiments, after reaching a desired diameter, a final coating that can provide lubricity to the body is applied. Any material that can provide lubricity may be used. An exemplary material is PTFE impregnated polyimide, silicone-based coatings, and hydrophilic based coatings.

Figure 15:
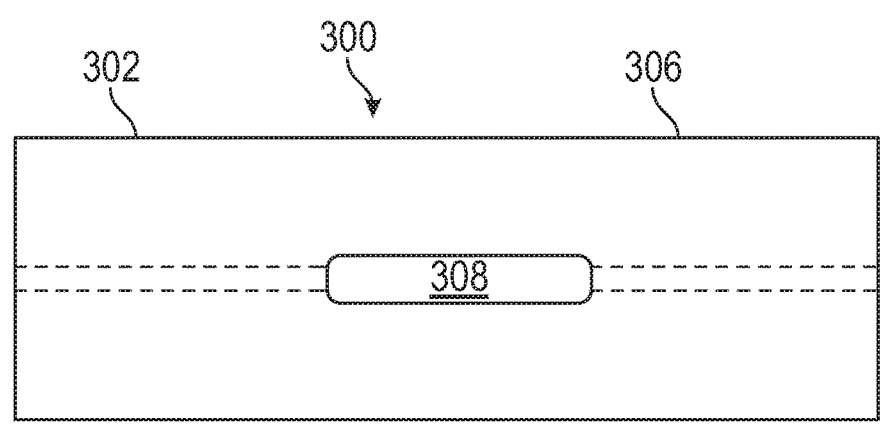
FIG. 15 shows an area of the conductive wire that has been exposed from the outer layer.

FIG. 15 shows an area of an embedded conductive wire 308 that has been exposed from the outer layer 306. As shown in FIG. 15, one or more sections of the outer layer 306 are modified to expose corresponding individual sections of the conductive wire 308. Any technique known in the art may be used to expose the sections of conductive wire 308. Exemplary techniques include chemical etching, mechanical cutting and shearing or laser ablation. In certain embodiments, as shown in FIG. 15, laser ablation is used to cut away the desired sections of outer layer 306 to expose the embedded conductive wire 308. Circumferential ablation may be utilized in some instances. Laser ablation of polymeric material is known in the art and accomplished by known techniques, such as those described in Kumagai (Applied Physics Letters, 65(14):1850-1852, 2004); Sutcliffe (Journal of Applied Physics, 60(9):3315-3322, 1986), and Blanchet et al. (Science, 262(5134):719-721, 1993), the content of each of which is incorporated by reference herein in its entirety. A reference ring at a proximal or distal end of the flexible elongate member 302 may be ablated to identify where the conductive wires 308 reside in the outer layer 306. In that regard, the distal end of the conductive wires may be ground to the specified grind profile for coupling directly or indirectly to the component 108. In that regard, in some instances the distal end of flexible elongate member 302 is coupled to a distal working end similar to those used in current sensing guidewires. In some particular instances, the flexible elongate member 302 is coupled to a distal section, intermediate section, and/or proximal section similar to those described in one or more of U.S. Pat. Nos. 5,125,137, 5,873,835, 6,106,476, 6,551,250, and U.S. patent application Ser. No. 13/931,052, filed Jun. 28, 2013, each of which is hereby incorporated by reference in its entirety.

Figure 16:
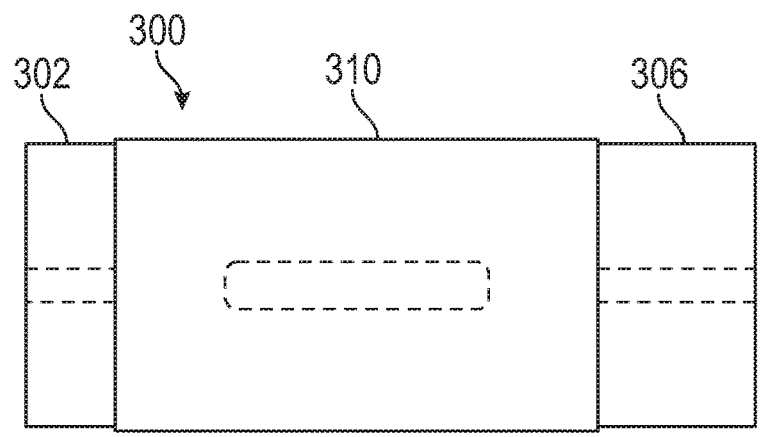
FIG. 16 shows a conductive material applied to an exposed area, covering the exposed section of conductive wire to create a conductive band that is already in contact with the conductive wires.

As shown in FIG. 16, a conductive material can then be applied to the flexible elongate member 302 over the exposed sections of the conductive wire 308. The conductive material covers the exposed sections of conductive wire 308 to define a conductive band 310 that is in contact with the exposed conductive wire 308. The conductive material will generally be a metal, such as gold. Numerous techniques are known in the art for apply the conductive material to the conductive wire. In certain embodiments, the conductive material is printed and sintered onto the exposed sections of conductive wires. Printing and sintering of metal is well known in the art. See for example, Kydd (U.S. Pat. Nos. 5,882,722 and 6,036,889), Karapatis et al. (Rapid Prototyping Journal, 4(2):77-89, 1998), and Kruth et al., (Assembly Automation, 23(4):357-371, 2003), the content of each of which is incorporated by reference herein in its entirety.

Figure 17:
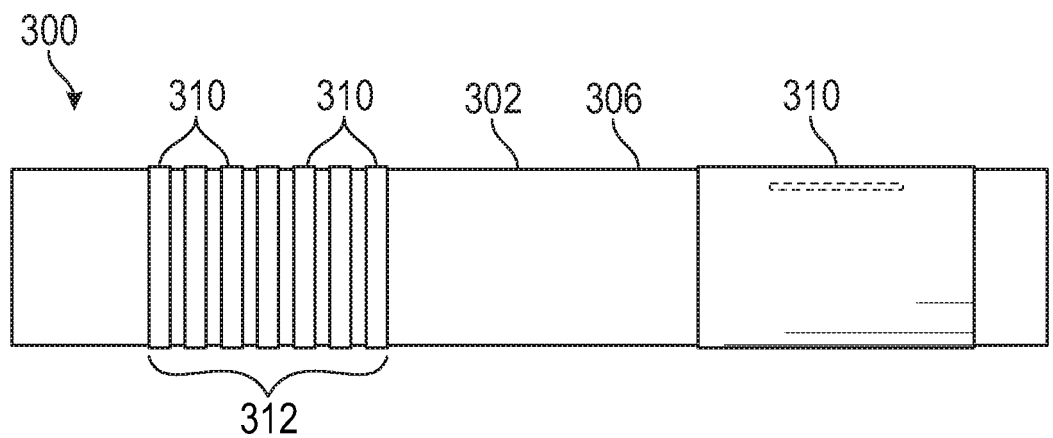
FIG. 17 shows two exemplary conductive band configurations.

Any desired pattern of conductive material may be placed onto the flexible elongate member 302. For example, the conductive bands can be solid, multiple rings, a spiral, or any other pattern that provides the optimum functionality. To that end, FIG. 17 shows two exemplary conductive band configurations. The configuration on the left shows a plurality of conductive bands 310 each connected to a common conductive wire 308 to define a connector 312, while the configuration on the right shows a solid conductive band 310 that defines a connector for another conductive wire 308 of the flexible elongate member.

Figure 18:
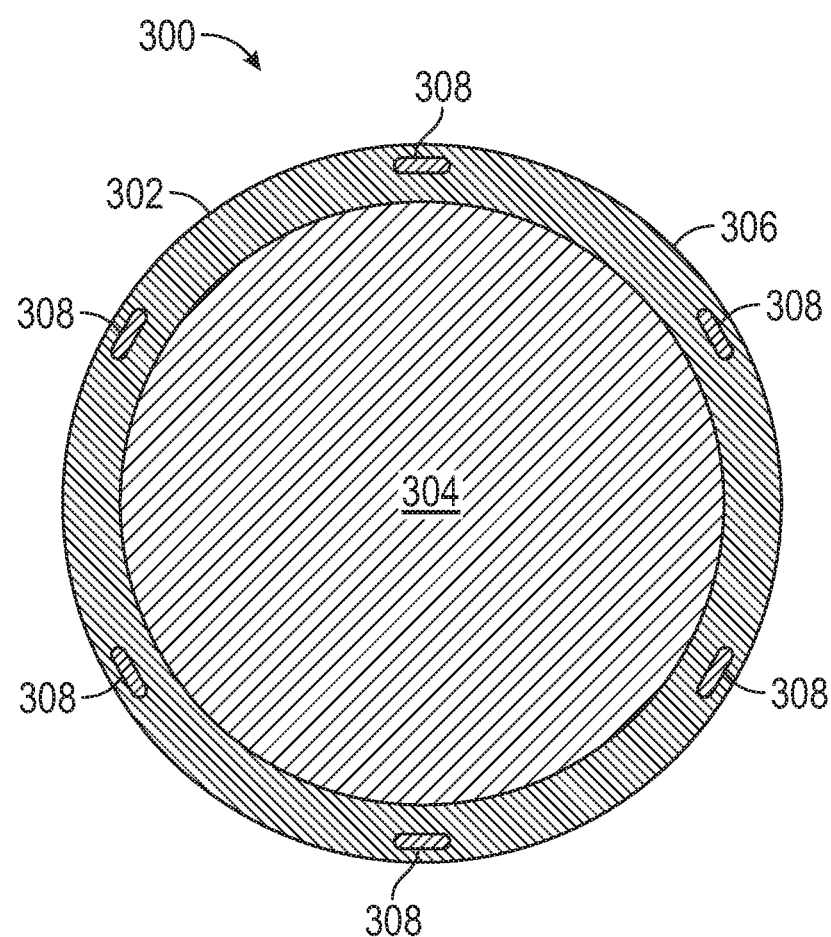
FIG. 18 shows a cross section of a guidewire having six conductive wires.

Guidewires of the invention are complete by communicatively coupling the component 108 to the conductive wires 308. In some particular instances, portions of the conductive wires 308 adjacent a distal end of the flexible elongate member 302 are electrically coupled to the component 108 either directly or indirectly, using soldering welding, one or more additional conductive members, leads, and/or other known techniques. In some instances, sections of the outer layer 306 are removed to expose the distal portions of the conductive wires 308 that will be coupled to the component 108. The component 108 can be mounted within a distal section of the flexible elongate member 302 using any suitable technique, including without limitation those disclosed in one or more of U.S. Pat. Nos. 5,125,137, 5,873, 835, 6,106,476, 6,551,250, U.S. patent application Ser. No. 13/931,052, filed Jun. 28, 2013, U.S. patent application Ser. No. 14/135,117, filed Dec. 19, 2013, U.S. patent application Ser. No. 14/137,364, filed Dec. 20, 2013, and U.S. patent application Ser. No. 14/139,543, filed Dec. 23, 2013, each of which is hereby incorporated by reference in its entirety As discussed above with respect to component 108, the sensor(s) of the intravascular device 300 provide a means to obtain intraluminal measurements within a body lumen and are connected to the one or more conductive bands on the intravascular device, which transmit and receive signals from the sensor(s). For example, the guidewire of the invention can include a pressure sensor, a flow sensor, a temperature sensor or combinations thereof. Preferably, the guidewire is a combination guidewire that includes both a pressure sensor and a flow sensor. Pressure sensors can be used to measure pressure within the lumen and flow sensors can be used to measure the velocity of blood flow. Temperature sensors can measure the temperature of a lumen. A guidewire with both a pressure sensor and a flow sensor provides a desirable environment in which to calculate fractional flow reserve (FFR) using pressure readings, and coronary flow reserve (CFR) using flow readings. Guidewires with two or more sensors can be made by increasing the number of conductive wires. For example, FIG. 18 shows a cross section of the flexible elongate member 302 having six conductive wires 308 embedded in the outer layer 306. In addition, the core 304 may also be utilized as a conductor in some embodiments. Such embodiments provide enough conductive pathways to facilitate the use of at least two sensors with the flexible elongate member 302.

The ability to measure and compare both the pressure and velocity flow and create an index of hyperemic stenosis resistance significantly improves the diagnostic accuracy of this ischemic testing. It has been shown that distal pressure and velocity measurements, particularly regarding the pressure drop-velocity relationship such as Fractional Flow reserve (FFR), Coronary flow reserve (CFR) and combined P-V curves, reveal information about the stenosis severity. For example, in use, the guidewire may be advanced to a location on the distal side of the stenosis. The pressure and flow velocity may then be measured at a first flow state. Then, the flow rate may be significantly increased, for example by the use of drugs such as adenosine, and the pressure and flow measured in this second, hyperemic, flow state. The pressure and flow relationships at these two flow states are then compared to assess the severity of the stenosis and provide improved guidance for any coronary interventions. The ability to take the pressure and flow measurements at the same location and same time with the combination tip sensor, improves the accuracy of these pressure-velocity loops and therefore improves the accuracy of the diagnostic information.

A pressure sensor allows one to obtain pressure measurements within a body lumen. A particular benefit of pressure sensors is that pressure sensors allow one to measure of fractional flow reserve (FFR) in vessel, which is a comparison of the pressure within a vessel at positions prior to the stenosis and after the stenosis. The level of FFR determines the significance of the stenosis, which allows physicians to more accurately identify hemodynamically relevant stenosis. For example, an FFR measurement above 0.80 indicates normal coronary blood flow and a non-significant stenosis. Another benefit is that a physician can measure the pressure before and after an intraluminal intervention procedure to determine the impact of the procedure.

A pressure sensor can be mounted, for example, on a distal portion of the guidewire. The pressure sensor can be formed of a crystal semiconductor material having a recess therein and forming a diaphragm bordered by a rim. A reinforcing member is bonded to the crystal and reinforces the rim of the crystal and has a cavity therein underlying the diaphragm and exposed to the diaphragm. A resistor having opposite ends is carried by the crystal and has a portion thereof overlying a portion of the diaphragm. Electrical conductor wires of the sensor are connected to a conductive band in the guidewire. Additional details of suitable pressure sensors that may be used with devices of the invention are described in U.S. Pat. No. 6,106,476. U.S. Pat. No. 6,106,476 also describes suitable methods for coupling the pressure sensor to a guidewire. Those methods are applicable to coupling the sensor to the conductive bands in guidewires of the invention.

In certain aspects, the guidewire of the invention includes a flow sensor. The flow sensor can be used to measure blood flow velocity within the vessel, which can be used to assess coronary flow reserve (CFR). The flow sensor can be, for example, an ultrasound transducer, a Doppler flow sensor or any other suitable flow sensor, disposed at or in close proximity to the distal tip of the guidewire. The ultrasound transducer may be any suitable transducer, and may be mounted in the distal end using any conventional method, including the manner described in U.S. Pat. Nos. 5,125,137, 6,551,250 and 5,873,835.

Additional features of the invention include proximal and distal tip coils or coverings.

Guidewires of the invention can be connected to an instrument, such as a computing device (e.g. a laptop, desktop, or tablet computer) or a physiology monitor, that converts the signals received by the sensors into pressure and velocity readings. The instrument can further calculate Coronary Flow Reserve (CFR) and Fractional Flow Reserve (FFR) and provide the readings and calculations to a user via a user interface.

Figure 19:
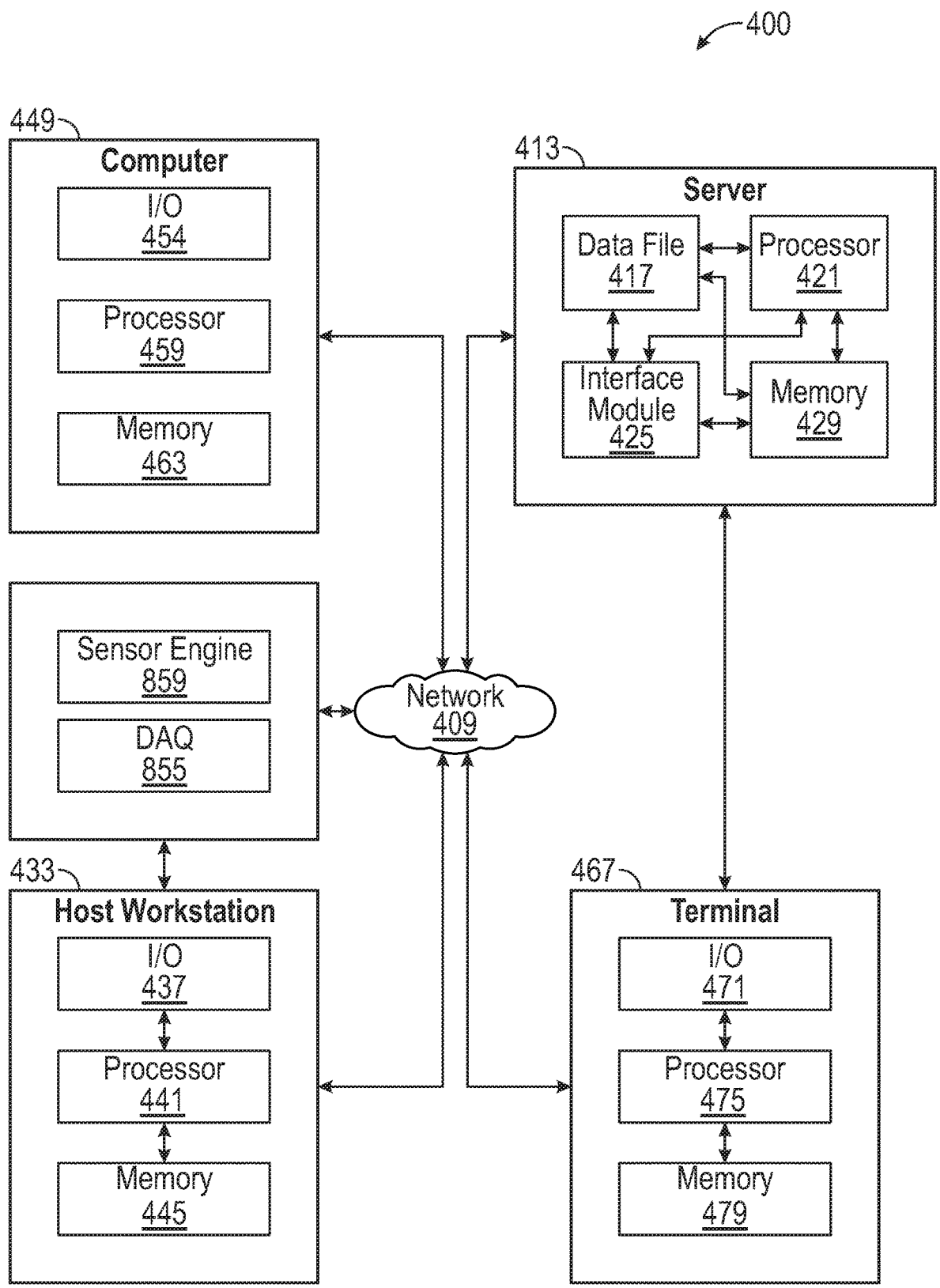
FIG. 19 is a system diagram according to certain embodiments.

In some embodiments, a user interacts with a visual interface to view images associated with the data obtained by the intravascular devices of the present disclosure. Input from a user (e.g., parameters or a selection) are received by a processor in an electronic device. The selection can be rendered into a visible display. An exemplary system including an electronic device is illustrated in FIG. 19. As shown in FIG. 19, a sensor engine 859 communicates with host workstation 433 as well as optionally server 413 over network 409. The data acquisition element 855 (DAQ) of the sensor engine receives sensor data from one or more sensors. In some embodiments, an operator uses computer 449 or terminal 467 to control system 400 or to receive images. An image may be displayed using an I/O 454, 437, or 471, which may include a monitor. Any I/O may include a keyboard, mouse or touchscreen to communicate with any of processor 421, 459, 441, or 475, for example, to cause data to be stored in any tangible, nontransitory memory 463, 445, 479, or 429. Server 413 generally includes an interface module 425 to effectuate communication over network 409 or write data to data file 417.

Processors suitable for the execution of computer program include, by way of example, both general and special purpose microprocessors, and any one or more processor of any kind of digital computer. Generally, a processor will receive instructions and data from a read-only memory or a random access memory or both. The essential elements of computer are a processor for executing instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. Information carriers suitable for embodying computer program instructions and data include all forms of non-volatile memory, including by way of example semiconductor memory devices, (e.g., EPROM, EEPROM, solid state drive (SSD), and flash memory devices); magnetic disks, (e.g., internal hard disks or removable disks); magneto-optical disks; and optical disks (e.g., CD and DVD disks). The processor and the memory can be supplemented by, or incorporated in, special purpose logic circuitry.

To provide for interaction with a user, the subject matter described herein can be implemented on a computer having an I/O device, e.g., a CRT, LCD, LED, or projection device for displaying information to the user and an input or output device such as a keyboard and a pointing device, (e.g., a mouse or a trackball), by which the user can provide input to the computer. Other kinds of devices can be used to provide for interaction with a user as well. For example, feedback provided to the user can be any form of sensory feedback, (e.g., visual feedback, auditory feedback, or tactile feedback), and input from the user can be received in any form, including acoustic, speech, or tactile input.

The subject matter described herein can be implemented in a computing system that includes a back-end component (e.g., a data server 413), a middleware component (e.g., an application server), or a front-end component (e.g., a client computer 449 having a graphical user interface 454 or a web browser through which a user can interact with an implementation of the subject matter described herein), or any combination of such back-end, middleware, and front-end components. The components of the system can be interconnected through network 409 by any form or medium of digital data communication, e.g., a communication network. Examples of communication networks include cell network (e.g., 3G or 4G), a local area network (LAN), and a wide area network (WAN), e.g., the Internet.

The subject matter described herein can be implemented as one or more computer program products, such as one or more computer programs tangibly embodied in an information carrier (e.g., in a non-transitory computer-readable medium) for execution by, or to control the operation of, data processing apparatus (e.g., a programmable processor, a computer, or multiple computers). A computer program (also known as a program, software, software application, app, macro, or code) can be written in any form of programming language, including compiled or interpreted languages (e.g., C, C++, Perl), and it can be deployed in any form, including as a stand-alone program or as a module, component, subroutine, or other unit suitable for use in a computing environment. Systems and methods of the invention can include instructions written in any suitable programming language known in the art, including, without limitation, C, C++, Perl, Java, ActiveX, HTML5, Visual Basic, or JavaScript.

A computer program does not necessarily correspond to a file. A program can be stored in a portion of file 417 that holds other programs or data, in a single file dedicated to the program in question, or in multiple coordinated files (e.g., files that store one or more modules, sub-programs, or portions of code). A computer program can be deployed to be executed on one computer or on multiple computers at one site or distributed across multiple sites and interconnected by a communication network.

A file can be a digital file, for example, stored on a hard drive, SSD, CD, or other tangible, non-transitory medium. A file can be sent from one device to another over network 409 (e.g., as packets being sent from a server to a client, for example, through a Network Interface Card, modem, wireless card, or similar).

Writing a file according to the invention involves transforming a tangible, non-transitory computer-readable medium, for example, by adding, removing, or rearranging particles (e.g., with a net charge or dipole moment into patterns of magnetization by read/write heads), the patterns then representing new collocations of information about objective physical phenomena desired by, and useful to, the user. In some embodiments, writing involves a physical transformation of material in tangible, non-transitory computer readable media (e.g., with certain optical properties so that optical read/write devices can then read the new and useful collocation of information, e.g., burning a CD-ROM).

In some embodiments, writing a file includes transforming a physical flash memory apparatus such as NAND flash memory device and storing information by transforming physical elements in an array of memory cells made from floating-gate transistors. Methods of writing a file are well-known in the art and, for example, can be invoked manually or automatically by a program or by a save command from software or a write command from a programming language.

Persons skilled in the art will also recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. A sensing guidewire, the guidewire comprising:
   a body comprising a proximal portion and a distal portion, the body further comprising a metallic inner core and an outer insulating layer surrounding and directly contacting the metallic inner core, wherein a first thickness of the metallic inner core is greater than a second thickness of the outer insulating layer, and wherein the metallic inner core is configured to facilitate handling for the sensing guidewire inside a vessel;
   a plurality of conductors embedded in the outer insulating layer and extending longitudinally and straight along a length of the body, wherein each of the plurality of conductors is a single component comprising a proximal portion and a distal portion;
   a connector region disposed at the proximal portion of the body, the connector region comprising:
      a plurality of conductive sections, wherein the proximal portion of each of the plurality of conductors is electrically coupled to a corresponding conductive section, wherein each conductive section is only a conductive material encircling the proximal portion of the body, wherein a surface of the corresponding conductor comprises an exposed portion exposed through an opening in the outer insulating layer, wherein the conductive material is positioned over the exposed portion of the surface of the corresponding conductor; and
   a sensor coupled to the distal portion of the body and electrically coupled to the distal portion of each of the plurality of conductors,
   wherein the outer insulating layer comprises a single layer insulating:
      the plurality of conductors and the plurality of conductive sections from the metallic inner core;
      the plurality of conductors from one another; and
      the plurality of conductive sections from one another, and
   wherein the outer insulating layer directly contacts each of the plurality of conductors and each of the plurality of conductive sections.

2. The guidewire according to claim 1, herein the guidewire is manufactured by a process including at least one of:
   printing each of the plurality of conductors using a conductive ink; or printing each of the plurality of conductive sections using the conductive ink.

3. The guidewire according to claim 1, wherein:
the opening extends a first amount in the longitudinal direction and a second amount in a circumferential direction perpendicular to the longitudinal direction,
the first amount is greater than the second amount, and
the opening is aligned with a corresponding straight and longitudinally-extending conductor.

4. The guidewire according to claim 3, wherein:
the second amount is greater than a width of the corresponding straight and longitudinally-extending conductor.

5. The guidewire according to claim 4, wherein each of the plurality of conductors comprises a ribbon conductor having a flat surface, and wherein the second amount is greater than the width of the corresponding ribbon conductor such that the entire flat surface of the corresponding ribbon conductor is in contact with the corresponding conductive section.

6. The guidewire according to claim 3, wherein a corresponding conductive section extends around the proximal portion of the body in the circumferential direction.

7. The guidewire according to claim 1, wherein the plurality of conductors is positioned around a circumference of the proximal portion of the body.

8. The guidewire according to claim 7, wherein the exposed portions of each of the plurality of conductors are longitudinally spaced from one another.

9. The guidewire according to claim 1, wherein the proximal portion of the body terminates at a proximal end, wherein the connector region further comprises a proximal end member at the proximal end of the body, and wherein a proximal-most conductive section of the plurality of conductive sections is spaced from the proximal end of the body by t proximal end member.

10. The guidewire according to claim 1, wherein the opening in the outer insulating layer extends longitudinally to expose the exposed portion of the corresponding conductor.

11. The guidewire according to claim 1, wherein:
each of the plurality of conductors is exposed through the outer insulating layer through a single corresponding opening in the outer insulating layer,
the openings corresponding to the plurality of conductors are disposed at different longitudinal positions, and
each of the conductors is electrically coupled to a single corresponding conductive section via the single corresponding opening in the outer insulating layer, each conductive section encircling the plurality of longitudinally-extending conductors at the proximal portion of the body.

12. The guidewire according to claim 1, wherein:
the plurality of conductors comprises a first conductor and a second conductor electrically coupled to the sensor, and
the plurality of conductive sections comprises a first conductive connection at a first longitudinal position and electrically coupled to the first conductor, and a second conductive section at a different second longitudinal position and electrically coupled to the second conductor.

13. The guidewire according to claim 1, wherein a circumferential portion of the conductive material directly contacts both the exposed portion of the surface of the corresponding conductor and the outer insulating layer adjacent to the exposed portion.

14. The guidewire according to claim 1, wherein the plurality of conductors extend from the proximal portion of the body to the distal portion of the body.

15. The guidewire according to claim 1, wherein each of the conductive sections comprises a conductive band composed of a single metallic material.

16. The guidewire according to claim 1, wherein the conductive material comprises gold.

17. The guidewire according to claim 1, wherein the outer insulating layer is composed of polyimide.

18. The guidewire according to claim 1, wherein the sensor is a pressure sensor.

19. The guidewire according to claim 18, wherein the pressure sensor comprises a crystalline semi-conductor material.

20. The guidewire according to claim 1, wherein the sensor is a flow sensor.

21. The guidewire according to claim 20, wherein the flow sensor comprises ultrasound transducer.

22. The guidewire according to claim 1, wherein the guidewire comprises a pressure sensor and a flow sensor.

23. A method for measuring a characteristic inside a vessel, the method comprising:
providing a sensing guidewire that comprises:
a body comprising a proximal portion and a distal portion, the body further comprising a metallic inner core and an outer insulating layer surrounding and directly contacting the metallic inner core, wherein a first thickness of the metallic inner core is greater than a second thickness of the outer insulating layer, and wherein the metallic inner core is configured to facilitate handling for the sensing guidewire inside a vessel;
a plurality of conductive wires embedded in the outer insulating layer and extending longitudinally and straight along a length of the body, wherein each of the plurality of conductive wires is a single component comprising a proximal portion and a distal portion;
a connector region disposed at the proximal portion of the body, the connector region comprising:
a plurality of conductive sections, wherein the proximal portion of each of the conductive wires is electrically coupled to a corresponding conductive section, wherein each conductive section is only a conductive material encircling the proximal portion of the body, wherein a surface of the corresponding conductive wire comprises an exposed portion exposed through an opening in the outer insulating layer, wherein the conductive material is positioned over the exposed portion of the surface of the corresponding conductive wire; and
a sensor coupled to the distal portion of the body and electrically coupled to the distal portion of each of the plurality of conductive wires,
wherein the outer insulating layer comprises a single layer insulating:
the plurality of conductive wires and the plurality of conductive sections from the metallic inner core;
the plurality of conductive wires from one another; and
the plurality of conductive sections from one another, and
wherein the outer insulating layer directly contacts each of the plurality of conductors and each of the plurality of conductive sections; and using the sensor to measure a characteristic while the sensing guidewire is positioned inside the vessel.

24. The method according to claim 23, wherein the sensor is a pressure sensor and the characteristic measured is intraluminal pressure.

25. The method according to claim 24, wherein the pressure sensor comprises a crystalline semi-conductor material.

26. The method according to claim 23, wherein the sensor is a flow sensor and the characteristic measured is intraluminal flow.

27. The method according to claim 26, wherein the flow sensor comprises an ultrasound transducer.

28. The method according to claim 23, wherein the sensing guidewire comprises a pressure sensor and a flow sensor.

29. The method according to claim 23, wherein the outer insulating layer is composed of polyimide.

* * * * *